United States Patent [19]

Köhler et al.

[11] Patent Number: 4,935,208

[45] Date of Patent: Jun. 19, 1990

[54] APPARATUS FOR RECEIVING A PLURALITY OF CARRIER ELEMENTS

[76] Inventors: Dora Köhler, Kreutzerweg 11, D1000 Berlin 45; Brigitte Hermann, Bronnbachergasse 18a, D-8700 Würzburg, both of Fed. Rep. of Germany

[21] Appl. No.: 239,791

[22] Filed: Sep. 1, 1988

[30] Foreign Application Priority Data

Sep. 1, 1987 [DE] Fed. Rep. of Germany ... 8711962[U]

[51] Int. Cl.$^5$ ................................................ B01L 9/00
[52] U.S. Cl. .................................. 422/104; 422/297; 422/300; 422/310; 435/287; 206/558; 206/564; 206/565; 206/593; 211/70.1; 211/126

[58] Field of Search ................ 422/104, 28, 292, 297, 422/300, 310; 435/287; 206/558, 564, 565, 593; 211/70.1, 126, 183

[56] References Cited

U.S. PATENT DOCUMENTS

| 4,541,992 | 9/1985 | Jerge et al. | 422/300 |
| 4,772,418 | 9/1988 | Leoncavallo | 422/310 |
| 4,782,942 | 11/1988 | Ashley et al. | 422/297 X |

Primary Examiner—Michael S. Marcus
Assistant Examiner—Lynn M. Kummert

[57] ABSTRACT

The present invention is directed to an apparatus for the insertion of carrier elements with comb-like titer strips into a microtiter plate and to provide a convenient holder for washing the titer strips. The apparatus provides a container and a changing insert with guide lamellas and space rods for holding the carrier elements.

11 Claims, 2 Drawing Sheets

APPARATUS FOR RECEIVING A PLURALITY OF CARRIER ELEMENTS

FIELD OF THE INVENTION

The present invention relates to containers for use in medical or chemical applications or the like and more particularly to devices for receiving a plurality of carrier elements holding plurality of titre strips or the like for experiments in medical fields such as serology.

BACKGROUND OF THE INVENTION

In numerous tests and experiments in medical fields such as serology, diverse types of liquid samples must be mixed with test reagents under predetermined conditions and measurements must be performed thereon after a predetermined reaction time. For conducting such serological tests and experiments, a device having a plurality of juxtaposed depressions arranged in a plastic card in which serum is brought into contact with antigens or antibodies, may be used. Microtiter plates are known in this connection.

To simply and economically conduct such experiments and tests with carriers coated with antigens or antibodies, a carrier, made from material such as nitrocellulose which comprises a strip-like holding member along whose longitudinal edge can be inserted in comblike manner a plurality of strips carrying antigens or similar test reagents, is preferred. The spacing between the strips correspond to spacing of depressions which are arranged in a matrix-like manner within a vessel frame. To conduct the actual tests, such carriers are secured to a vessel frame with test strips engaging the frame by a series of depressions. In this manner, serological samples and the antigens on strip affixed to a carrier may be reacted within a row of depressions.

Unfortunately, if a plurality of linearly juxtaposed carriers are placed on vessel frames, they could not be non-interchangeably locked with sufficient precision for the requisite reaction time. Moreover, since the container arrangement remained substantially open at the top, the requisite constant conditions could not be obtained during the reaction sequence.

Accordingly, it is an object of the present invention to further develop and improve devices for receiving carrier elements.

Another object of the invention is to provide a device which will maintain the requisite constant reaction conditions for serological tests and experiments and the like.

Additionally, an object of the invention is to provide adequate locking means, wherein the individual sample components lie within a closed volume.

SUMMARY OF THE INVENTION

To achieve these and other objects of the invention, an apparatus for receiving a plurality of carrier elements which hold, in comblike manner, a plurality of titre strips or the like, is disclosed. The titre strips can be inserted into separate test compartments within a vessel frame, such as a microtitre plate. The apparatus generally comprises a wetting tank, having a cross-sectionally rectangular container with a supporting flange along its perimeter, a changing insert having guide lamellas arranged along a longitudinal direction of the wetting tank insert slots for carrier elements and a lid passing over the wetting tank and the changing insert to sealingly close the apparatus.

BRIEF DESCRIPTION OF THE DRAWINGS

The invention will be described in greater detail hereinafter by way of reference to the following drawings, in which.

DETAILED DESCRIPTION OF THE PREFERRED EMBODIMENT

Figure 1:
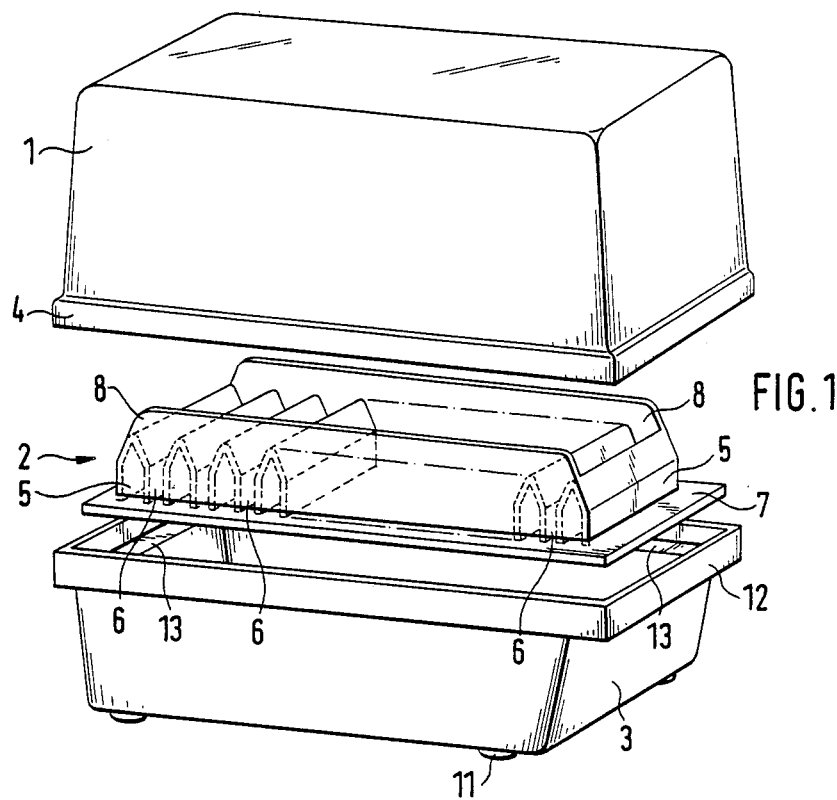
FIG. 1 is a perspective view, exploded view of the apparatus for receiving a plurality of carrier elements.

Referring to the figures, wherein like numerals represent identical elements throughout the several views, an apparatus for receiving a plurality of carrier elements is shown in FIG. 1, generally comprising lid 1, changing insert 2 and wetting tank 3. Lid 1 is provided with a closing edge 4. Wetting tank 3 has substantially vertical walls and marginal flange 12 along its perimeter near top portion of vertical walls. The closing edge 4 of lid 1 overlaps the marginal flange 12 of the wetting tank 3 to form a secure seal. Connected as a singular unit to the marginal flange is an all-round supporting strip 13 running along the inside perimeter of and extending horizontally into wetting tank 3. Supporting strip 13 of marginal flange 12 receives and locks changing insert 2, whose slotted plate 7 may be inserted in a dimensionally adapted manner into marginal flange 12.

Figure 2:
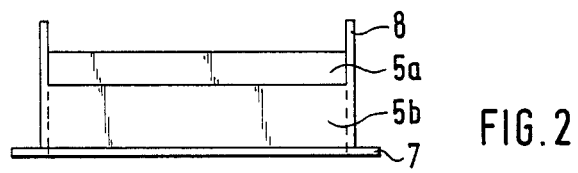
FIG. 2 is a cross sectional view of the changing insert.

Changing insert 2 comprises a plurality of guide lamellas 5 extending vertically upward from slotted plate 7. The length of guide lamellas 5 extend substantially the width of slotted plate 7 terminating at a predetermined distance from edge of said plate 7. Thus, border for plate 7 is created between edges of the guide lamellas 5 and edge of slotted plate 7. The cross-section of each guide lamella 5, as shown in FIG. 2, is similar to the gable shape of a house and comprises upper, tapering, conical guide portion 5a and slotted guide portion 5b connected thereto and extending downward to slotted plate 7.

Figure 3:
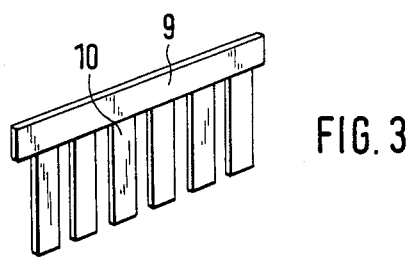
FIG. 3 is a perspective view of a comblike carrier element to be inserted in slot inserts of guide lamellas.
Figure 2A:
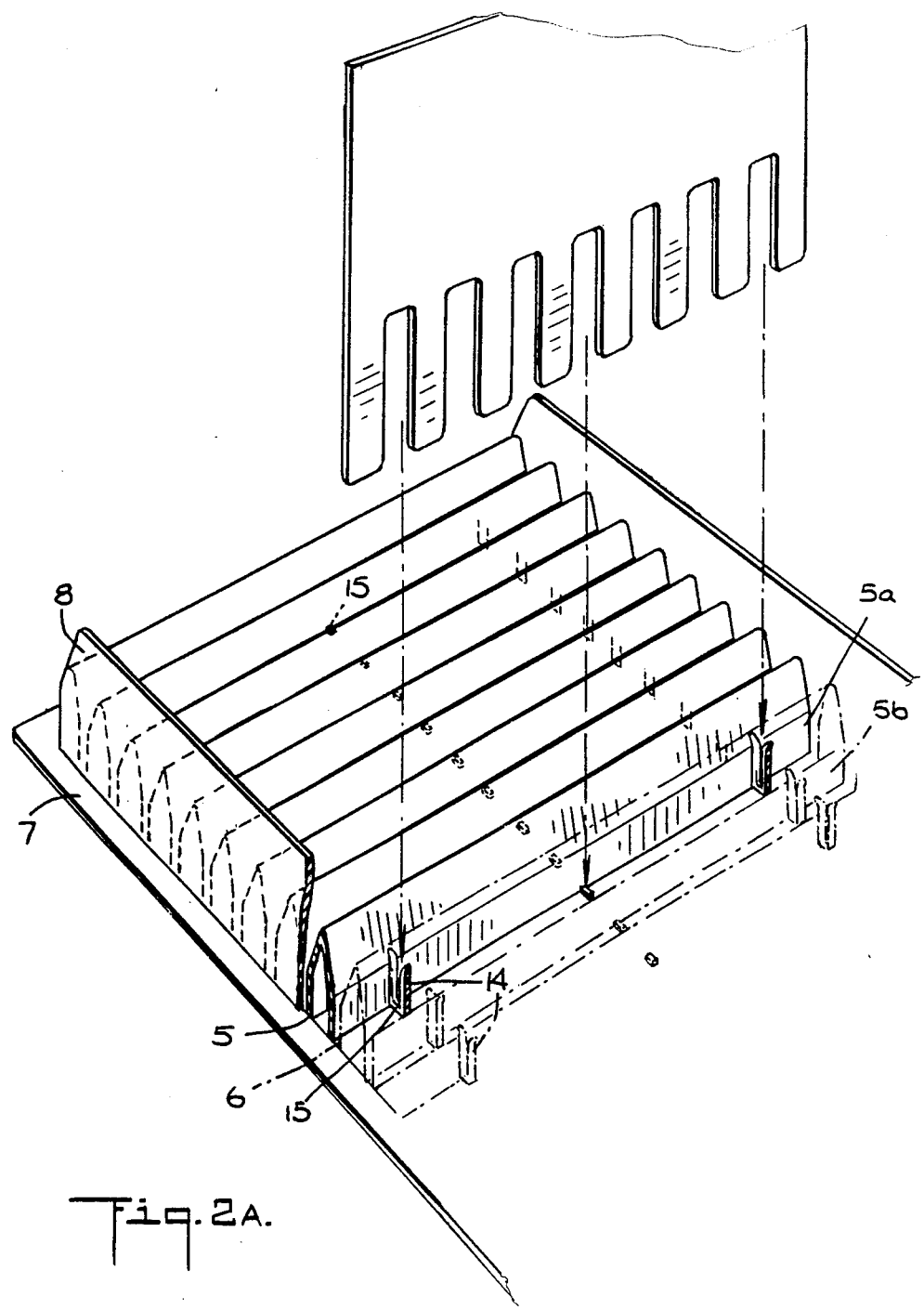
FIG. 2A is a perspective view of the changing insert showing the spaced rods which forms a web with the guide lamellas.

Conical guide portion 5a allows the introduction of comblike carrier elements shown in FIG. 3 into changing insert 2, while slotted guide 5b defines insert slot 6 between adjacent guide lamellas 5, whose width is adapted to thickness of comblike carrier elements 10 or the upper mounting support 9 thereof. The introduction of carrier elements is facilitated by this conical construction.

The conical guide portion 5a passes in the direction of insertion downwards into a substantially parallel slot guide, which in turn defines a position for each carrier element 10 within the associated insert slot. The comblike carrier elements may be removed from the apparatus individually with the changing frame. The wetting tank 3 then becomes immediately available for the next test series. Furthermore, the carrier elements 10 are laterally and cohesively secured within the insert slots 6 of the guide lamellas 5 which have side walls 8 on their two sides, as well as sides along their frontal end faces. The height of these side walls 8 adequately pass over that of the guide lamellas. To further facilitate insertion of carrier elements and to better retain them within insert slot 6, slotted guides 5b may be fitted with additional vertical guide studs 14.

At lower end of insert slot 6, in vicinity of slotted plate 7, spaced rods 15 running in the longitudinal direction of changing insert 2 engages the insert, to further secure it. Thus, following introduction of carrier elements into insert slots 6, holding strips rest on the webs formed by the insert slot 6 and the space rods 15 and the insertion depth of the carrier elements 10 is consequently delineated.

After inserting guide lamellas 5 equipped with comb-like carrier elements 10 and changing insert 2 into wetting tank 3, lid 1 having a closing edge 4 engages over marginal flange 12 to securely seal the apparatus. Because lid 1 passes over the changing insert 2 within wetting tank 3 as well as the tank 3 itself, the titre strips on the carrier elements 10 which are brought into reaction engagement with the test media within the test compartments in the microtitre plate are not subject to changes in the physical parameters such as moisture, temperature, chemical conditions for the duration of the test. The flange of the wetting tank locks the changing insert and simultaneously serves to receive the microtitre plate or the like.

The bottom of wetting tank 3 are equipped with feet 11. Microtitre plates may also be received by the changing insert 2.

While the preferred embodiment and technique of the invention has been presented in detail, modifications and adaptations of such technique and embodiment will be apparent to those skilled in the art. However, it is to be expressly understood that such modifications and adaptations are within the spirit and scope of the present invention as set forth in the following claims. For example, other advantages and details of the invention are described in the preferred embodiment which can be particularly advantageously used in conjunction with immune diagnosis. The present apparatus is suitable for the most varied test series and therefore for a wide range of uses and should not be limited to the field of human medicine, immune diagnosis and can also be used for animal diagnosis, as well as in tests and research in the biological field.

I claim:

1. An apparatus for receiving a plurality of carrier elements having a plurality of titer strips in a comb-like manner for introduction into a microtiter plate containing test compartments, said apparatus comprising:

a wetting tank with a supporting strip along the top edge extending substantially horizontally into the wetting tank;

a changing insert with laterally placed guide lamellas and longitudinally spaced rods to form insert slots for the carrier elements, said changing insert having a horizontal ledge arranged to rest on said supporting strip;

a cover means to removably and sealingly engage the wetting tank and enclose the changing insert.

2. The apparatus of claim 1, wherein said cover means is a lid.

3. The apparatus of claim 1, wherein said wetting tank has a rectangular cross-section.

4. The apparatus of claim 3, wherein ends of the guide lamellas at a distance from an edge of the slotted plate are bounded by side walls engaging the guide lamellas over the height of the lamellas.

5. The apparatus of claim 1, wherein ends of the guide lamellas at a distance from an edge of the slotted plate are bounded by side walls engaging the guide lamellas over the height of the lamellas.

6. The apparatus of claim 1, wherein said changing insert, comprises:

a slotted plate; and vertically upwardly directed guide lamellas located on and integral with components of the slotted plate.

7. The apparatus of claim 6, wherein ends of the guide lamellas at a distance from an edge of the slotted plate are bounded by side walls engaging the guide lamellas over the height of the lamellas.

8. The apparatus of claim 6 wherein each of said guide lamellas, cross-sectionally, comprises:

an upwardly tapering, conical guide portion; and a bottom portion with a plurality of slotted guides connected thereto defining therebetween a guide for insertion of each carrier element.

9. The apparatus of claim 8, wherein ends of the guide lamellas at a distance from an edge of the slotted plate are bounded by side walls engaging the guide lamellas over the height of the lamellas.

10. The apparatus of claim 1 wherein each of said guide lamellas, cross-sectionally, comprises:

an upwardly tapering, conical guide portion; an a bottom portion with a plurality of slotted guides connected thereto and defining therebetween a guide for the insertion of a titer strip of the carrier element.

11. The apparatus of claim 10, wherein ends of the guide lamellas at a distance from an edge of the slotted plate are bounded by side walls engaging the guide lamellas over the height of the lamellas.

* * * * *